United States Patent [19]

Mizutani et al.

[11] 4,366,311
[45] Dec. 28, 1982

[54] NOVEL DIANEMYCIN DERIVATIVE

[75] Inventors: Taku Mizutani, Ageo; Michio Yamagishi, Tokorozawa; Kazutoshi Mizoue, Urawa; Akira Kawashima, Tokyo; Sadafumi Omura, Ageo; Noboru Otake, Yokohama; Haruo Seto, Hachioji, all of Japan

[73] Assignee: Taisho Pharmaceutical Co., Ltd., Tokyo, Japan

[21] Appl. No.: 303,497

[22] Filed: Sep. 18, 1981

[30] Foreign Application Priority Data

Sep. 27, 1980 [JP] Japan ............................. 55-134814

[51] Int. Cl.³ .............................................. C07H 3/06
[52] U.S. Cl. ..................................... 536/123; 424/180
[58] Field of Search ................... 536/1, 17 R; 424/181

[56] References Cited

U.S. PATENT DOCUMENTS 3,577,531  5/1971  Gorman et al. ................. 424/122
4,138,481  2/1979  Martin et al. ................... 536/17 R
4,263,427  4/1981  Liu et al. ........................ 424/181
4,269,971  5/1981  Yamagishi et al. ............. 536/17 R
4,302,450  11/1981  Camai et al. .................... 424/181

OTHER PUBLICATIONS

Hamill et al., "Jour. of Antibiotics", vol. 22, No. 4, pp. 161–164, 1969.
Mizutani et al., "Jour. of Antibiotics", vol. 33, No. 2, pp. 137–143, 1980.

Primary Examiner—Johnnie R. Brown
Attorney, Agent, or Firm—Kenway and Jenney

[57] ABSTRACT

A novel compound of the formula

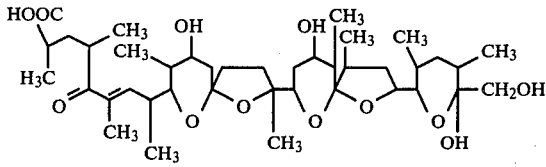

and the salts thereof, derived from dianemycin, are useful as antiprotozoal and antibacterial agents.

1 Claim, No Drawings

NOVEL DIANEMYCIN DERIVATIVE

BACKGROUND

Dianemycin, from which the novel compound of the present invention is prepared, is a polyether antibiotic described in U.S. Pat. No. 3,577,531, Journal of Antibiotics, 22, 161 (1969), and ibid., 33, 137 (1980). This antibiotic has activity against protozoa such as coccidiosis and against Gram positive bacteria, and is represented by the formula

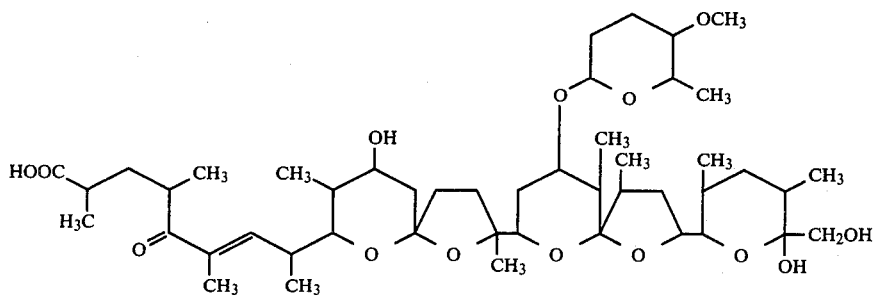

DESCRIPTION AND PREFERRED EMBODIMENTS

The present invention relates to a novel derivative of dianemycin. More particularly, the present invention is concerned with the novel compound (hereinafter referred to as compound I) of the formula

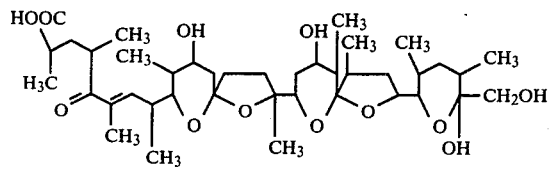

and the salts thereof.

The salts of compound I include the corresponding alkali metal salts such as sodium and potassium salts, alkaline earth metal salts, and ammonium salt. Most preferred are the sodium salt and potassium salt in view of ease in handling.

As a result of various studies in attempts to find compounds having improved properties as compared with dianemycin of which the use in therapy is extremely restricted by the high toxicity, compound I has been found to show the diminished toxicity together with valuable antiprotozoal activity and antibacterial activity against Gram positive bacteria. The present invention is based on the above finding.

Accordingly, an object of the present invention is to provide compound I and the salts thereof which have desired inhibitory activity and show much less toxicity than dianemycin.

Compound I or a salt thereof may be prepared as follows: In an organic solvent such as acetone, acetonitrile or chloroform is dissolved dianemycin or a salt thereof such as an alkali metal, an alkaline earth metal or ammonium salt. The resulting solution, after adjustment of the pH to about 3 with p-toluenesulfonic acid, is allowed to stand at room temperature to give compound I. Compound I is converted to its sodium salt in a conventional manner and extracted with an organic solvent such as benzene, ethyl acetate or chloroform. The extract is concentrated to dryness and then again dissolved in a suitable organic solvent (i.e., chloroform, methanol and a mixture thereof). Purification by appropriately combined procedures of silica gel column chromatography and gel filtration, and recrystallization from a mixed solvent of methanol and water give compound I sodium salt as prismatic crystals.

Compound I may be obtained by treating the sodium salt thus obtained in a conventional manner. The desired salt of compound I may be obtained by treating compound I in a conventional manner.

Dianemycin, the starting material for preparation of compound I, may be produced by culturing *Streptomyces hygroscopicus*, for example, *Streptomyces hygroscopicus* TM-531 described in Journal of Antibiotics, 33, 137 (1980) and U.S. Pat. No. 4,269,971, which has been deposited under the name of Streptomyces TM-531 at Fermentation Research Institute, Agency of Industrial Science and Technology, Japan, as FERM-P 4737 on Nov. 29, 1978 and at American Type Culture Collection, as ATCC 31590.

Compound I and the salts thereof thus obtained have the excellent activity against protozoa, especially toxoplasma, and against Gram positive bacteria. Decreased toxicity is an important advantage provided by compound I and the salts thereof. Thus, compound I and the salts thereof can be used as antiprotozoal agents and antibacterial agents in animals including humans.

For the control of coccidiosis in poultry, a nontoxic anticoccidial amount of the compound of the present invention is administered to the birds, preferably orally on a daily basis. In case of the oral administration, compound I or the salts thereof may be supplied with a substance capable of being consumed by the birds, preferably the feed of the birds.

The rate of administration, which is effective against infection of coccidiosis, is generally in the range of from 100 to 700 ppm, preferably 250 to 500 ppm, by weight of unmedicated feed. The compounds of the present invention may be used optionally together with other anticoccidial agents.

The following "Test Examples" are illustrative of the physiological effects of the compound of the present invention.

TEST EXAMPLE 1

Normal ICR mice were intraperitoneally injected with 1 ml of a sterilized 0.2% solution of glycogen in saline solution and, after 5 days, intraperitoneally injected with 5 ml of a Hank's solution containing heparin to collect macrophage.

After centrifugation and washing, the macrophage was diluted with a medium of TC-199 containing 20% of calf serum so that the resulting solution contained about $10^6$ cells/ml of macrophage. 1 ml of this suspension was pipetted into a cultivation Petri dish containing circular cover glass of 1.5 cm in diameter, followed by cultivation for 24 hours in an incubator containing 5% of carbon dioxide.

$5 \times 10^5$ toxiplasma RH strain collected on the 2nd day after intraperitoneal infection of mice were brought into contact with the thus cultivated macrophage at 37° C. for about 1 hour, and non-infecting toxiplasma RH strain were washed away using the same medium followed by adding thereto the same medium.

A drug-containing group was prepared by adding compound I sodium salt to the medium so that the final concentration of the compound became 0.1 ppm.

Medical effects were evaluated as follows; After cultivation at 37° C. for 48 hours, May-Grünwald/Giemsa double straining was conducted to determine the percentage of macrophage cells containing therein 1 to 5 toxoplasma or 6 or more toxoplasma, thus the infected control group was compared with the drug-added group.

The results thus obtained are shown in Table 1.

TABLE 1

| | Anti-toxoplasma Effect | |
|---|---|---|
| | Percentage of Toxoplasma-infected Macrophage | |
| | 1 to 5 Toxoplasma/cell | 6 or more Toxoplasma/cell |
| Infected Control Group | 30.8 | 31.8 |
| Compound I Sodium Salt-Added Group | 0 | 0 |

(Note)
Observation under an optical microscope revealed no cytotoxic effect by the addition of compound I sodium salt.

TEST EXAMPLE 2

MIC (Minimum Inhibitory Concentration) was measured according to the method specified by the Chemotherapeutic Society using a heat infusion agar medium containing compound I sodium salt, to examine antibacterial effects of the compound. The results thus obtained are shown in Table 2.

TABLE 2

| Antibacterial Effects | |
|---|---|
| Tested Bacteria | MIC (mcg/ml) |
| *Staphylococcus aureus* FDA 209 P | 25 |
| *Staphylococcus aureus* Smith | 50 |
| *Staphylococcus aureus* TPR-23 | 50 |
| *Staphylococcus epidermidis* TPR-25 | 50 |
| *Staphylococcus epidermidis* IID 866 | 50 |
| *Streptococcus faecalis* ATCC 8043 | 50 |
| *Bacillus subtilis* ATCC 6633 | 25 |
| *Bacillus licheniformis* | 12.5 |
| *Escherichia coli* NIHJ C-2 | >200 |

TEST EXAMPLE 3

Compound I sodium salt and the control drug of dianemycin sodium salt were respectively suspended in a 5% solution of gum arabic in saline solution.

Two groups of 7 ddY strain male mice (4-week old) were intraperitoneally injected with each of the above-described drug suspension. $LD_{50}$ values (mg/kg) of the compounds were determined from the total mortality per group for 7 consecutive days to examine the acute toxicity.

The results thus obtained are shown in Table 3.

TABLE 3

| Tested Drug | $LD_{50}$ (mg/kg) |
|---|---|
| Dianemycin Sodium Salt | 7.2 |
| Compound I Sodium Salt | 191 |

The following "Reference Example" and "Examples" are illustrative of the source material dianemycin and the compounds of the present invention, respectively.

REFERENCE EXAMPLE

A sterilized liquid medium comprising 2% glucose, 2% oatmeal, 0.3% beef extract, 0.3% sodium chloride, 0.25% calcium carbonate, 0.04% ferric sulfate and 0.04% manganese chloride was inoculated with TM-531 strain, and the inoculated strain was aerobically cultivated at 30° C. for 72 hours with stirring to produce a seed culture.

200 l of a sterile medium having the same composition as above charged in a 250 l-fermentation tank was inoculated with 5 l of the seed culture prepared as above and the culture was aerobically cultivated at 30° C. for 72 hours with stirring. After completion of the cultivation, the resulting fermentation broth was centrifuged to separate the broth into a supernatant and microbial cells. The supernatant thus obtained was extracted with three portions of ethyl acetate and the combined extracts were set aside. The microbial cells were extracted with two 15 l-portions of acetone and the combined acetone extract was concentrated until acetone was distilled out and further extracted with ethyl acetate. The resulting extract was combined with the above ethyl acetate extract and the combined extracts were concentrated under reduced pressure to obtain about 112 g of a brown syrup. The whole amount of the syrup was dissolved in 500 ml of benzene and the solution was adsorbed on a silica gel column [Wako Gel C-200 (trade name; made by Wako Junyaku K.K.)] which had been treated with benzene.

The column was eluted first with benzene and then with benzene-acetone (90:10) and the eluate was discarded. The column was subsequently eluted with benzene-acetone (50:50) and the fractions thus obtained were collected and concentrated to a dryness under reduced pressure. The resulting crude product was dissolved in acetone. The acetone solution was gel-filtered on Sephadex LH-20 (trade name; made by Pharmacia Co.) with acetone and the resulting active fraction was concentrated to dryness under reduced pressure to obtain 34 g of a light yellow powder.

Recrystallization of the product from acetone-water (2:1) yielded 26 g of dianemycin as needle crystals.

EXAMPLE 1

1 g of dianemycin was dissolved in 70 ml of acetonitrile, and 250 mg of p-toluenesulfonic acid was added thereto. After stirring the mixture to the point of dissolution, the resulting solution was allowed to stand at room temperature to react overnight.

An aqueous solution of sodium bicarbonate was added to the reaction solution to adjust the pH to 8 and, after allowing to stand for 30 minutes, the solution was extracted twice with 50 ml of benzene. The extracts were combined, washed with water, dried over anhydrous sodium sulfate, and concentrated to dryness to obtain 0.86 g of a crude powder of compound I sodium salt.

EXAMPLE 2

1 g of dianemycin sodium salt was dissolved in 70 ml of acetonitrile, and 300 mg of p-toluenesulfonic acid was added thereto. After stirring the mixture to the point of dissolution, the solution was allowed to stand at room temperature to react overnight. An aqueous solution of sodium bicarbonate was added to this reaction solution to adjust the pH 8 and, after allowing to stand for 30 minutes, the solution was extracted twice with 50 ml of benzene. The extracts were combined, washed with water, dried over anhydrous sodium sulfate, and concentrated to dryness to obtain 0.83 g of a crude powder of compound(I) sodium salt.

EXAMPLE 3

The crude products of compound I sodium salt obtained in Examples 1 and 2 were combined, dissolved in 5 ml of a mixed solvent of chloroform-methanol (49:1), adsorbed on 100 ml of silica gel column [Wako Gel C-200 (trade name; made by Wako Junyaku K.K.)] packed with the mixed solvent described above, and eluted with the solvent.

Eluate fractions from 250 to 400 ml [confirmed by thin layer chromatography (chloroform:methanol=9:1)] were collected and concentrated to dryness. The resulting residue was dissolved in a small amount of methanol and was subjected to gel filtration with methanol using Sephadex LH-20 (trade name; made by Pharmacia Co.).

Active fractions were collected and concentrated to dryness, and crystallization of the residue from a mixed solvent of methanol-water (2:1) gave 0.55 g of compound I sodium salt as colorless prismatic crystals.

m.p. 203°–205° C.

Specific rotatory power: $[\alpha]_D^{26} = +42°$ (c=0.5, methanol)

UV absorption spectrum (methanol): $E_1{}_{cm}^{1\%}$ (232 nm)=163.8

Elemental analysis: Calcd. for $C_{40}H_{65}O_{12}Na$: C, 63.16; H, 8.55; Na, 3.03. Found: C, 63.10; H, 8.66; Na, 2.99.

What is claimed is:

1. A compound of the formula

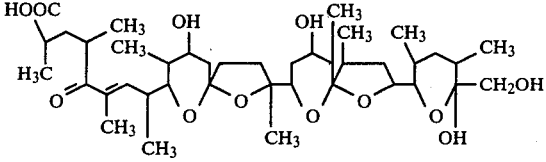

and the alkali metal, alkaline metal and ammonium salts thereof.

* * * * *